(12) United States Patent
Grasso et al.

(10) Patent No.: US 7,335,514 B2
(45) Date of Patent: Feb. 26, 2008

(54) OPTICAL BIOSENSOR

(75) Inventors: Valentina Grasso, Carignano (IT);
Federica Valerio, Orbassano (IT); Vito Guido Lambertini, Giaveno (IT);
Marco Pizzi, Turin (IT); Piero Perlo, Sommariva Bosco (IT)

(73) Assignee: CRF Societa Consortile per Azioni, Turin (IT)

( * ) Notice: Subject to any disclaimer, the term of this patent is extended or adjusted under 35 U.S.C. 154(b) by 0 days.

(21) Appl. No.: 10/858,370

(22) Filed: Jun. 2, 2004

(65) Prior Publication Data

US 2005/0019799 A1 Jan. 27, 2005

(30) Foreign Application Priority Data

Jun. 3, 2003 (IT) .......................... TO2003A0409

(51) Int. Cl.
*G01N 33/553* (2006.01)
(52) U.S. Cl. ...................... 436/525; 436/518; 436/524; 435/7.1; 435/283.1; 435/287.1; 435/287.2; 435/288.3
(58) Field of Classification Search ................. 422/50, 422/55–58, 61, 68.1, 82.01, 82.02, 82.03, 422/82.04, 82.05; 435/4, 7.1, 287.1, 287.2, 435/287.9, 288.4, 288.6, 283.1, 288.3; 436/501, 436/518, 524, 525, 528
See application file for complete search history.

(56) References Cited

U.S. PATENT DOCUMENTS

| | | | |
|---|---|---|---|
| 4,889,631 A * | 12/1989 | Rigby et al. .............. 210/493.1 |
| 5,285,078 A * | 2/1994 | Mimura et al. ................ 257/3 |
| 5,389,524 A * | 2/1995 | Larsen et al. .................. 435/29 |
| 5,922,183 A * | 7/1999 | Rauh ........................ 204/403.1 |
| 5,946,600 A * | 8/1999 | Hurwitz et al. ............. 438/688 |
| 6,207,369 B1 * | 3/2001 | Wohlstadter et al. .......... 435/6 |
| 6,229,158 B1 * | 5/2001 | Minemier et al. ............. 257/81 |
| 6,248,542 B1 * | 6/2001 | Rider et al. .................. 435/7.2 |
| 6,288,390 B1 * | 9/2001 | Siuzdak et al. ............. 250/288 |
| 6,355,420 B1 * | 3/2002 | Chan .............................. 435/6 |
| 6,464,853 B1 * | 10/2002 | Iwasaki et al. ............. 205/118 |
| 6,471,136 B1 | 10/2002 | Chatterjee et al. |
| 6,666,214 B2 * | 12/2003 | Canham ..................... 128/899 |
| 6,726,818 B2 * | 4/2004 | Cui et al. .............. 204/403.01 |
| 6,803,581 B2 * | 10/2004 | Prince et al. ................ 250/372 |
| 6,803,704 B2 * | 10/2004 | Motoi et al. ............ 313/103 R |
| 2002/0034646 A1 | 3/2002 | Canham |
| 2002/0061534 A1 * | 5/2002 | Ogura ............................ 435/6 |
| 2002/0094533 A1 * | 7/2002 | Hess et al. ..................... 435/6 |
| 2004/0040868 A1 * | 3/2004 | DeNuzzio et al. .......... 205/792 |
| 2004/0115707 A1 * | 6/2004 | Amano .......................... 435/6 |
| 2004/0175710 A1 * | 9/2004 | Haushalter ..................... 435/6 |

FOREIGN PATENT DOCUMENTS

| EP | 1 182 456 A2 | 2/2002 |
|---|---|---|
| EP | 1 182 456 A3 | 2/2002 |

* cited by examiner

*Primary Examiner*—Long V. Le
*Assistant Examiner*—Melanie J. Yu
(74) *Attorney, Agent, or Firm*—Sughrue Mion, PLLC

(57) ABSTRACT

The present invention relates to an optical biosensor comprising a porous matrix. In the specific case, reference is made to anodized porous alumina, on the surface of which the biological component specific for the analyte in question is immobilized, and to an optical-signal detector connected to said matrix. The present patent further relates to a biosensor having the porous matrix and the optical detector integrated in a single structure, in particular to biosensors with porous matrix other than porous alumina, for example porous silicon.

12 Claims, 4 Drawing Sheets a b

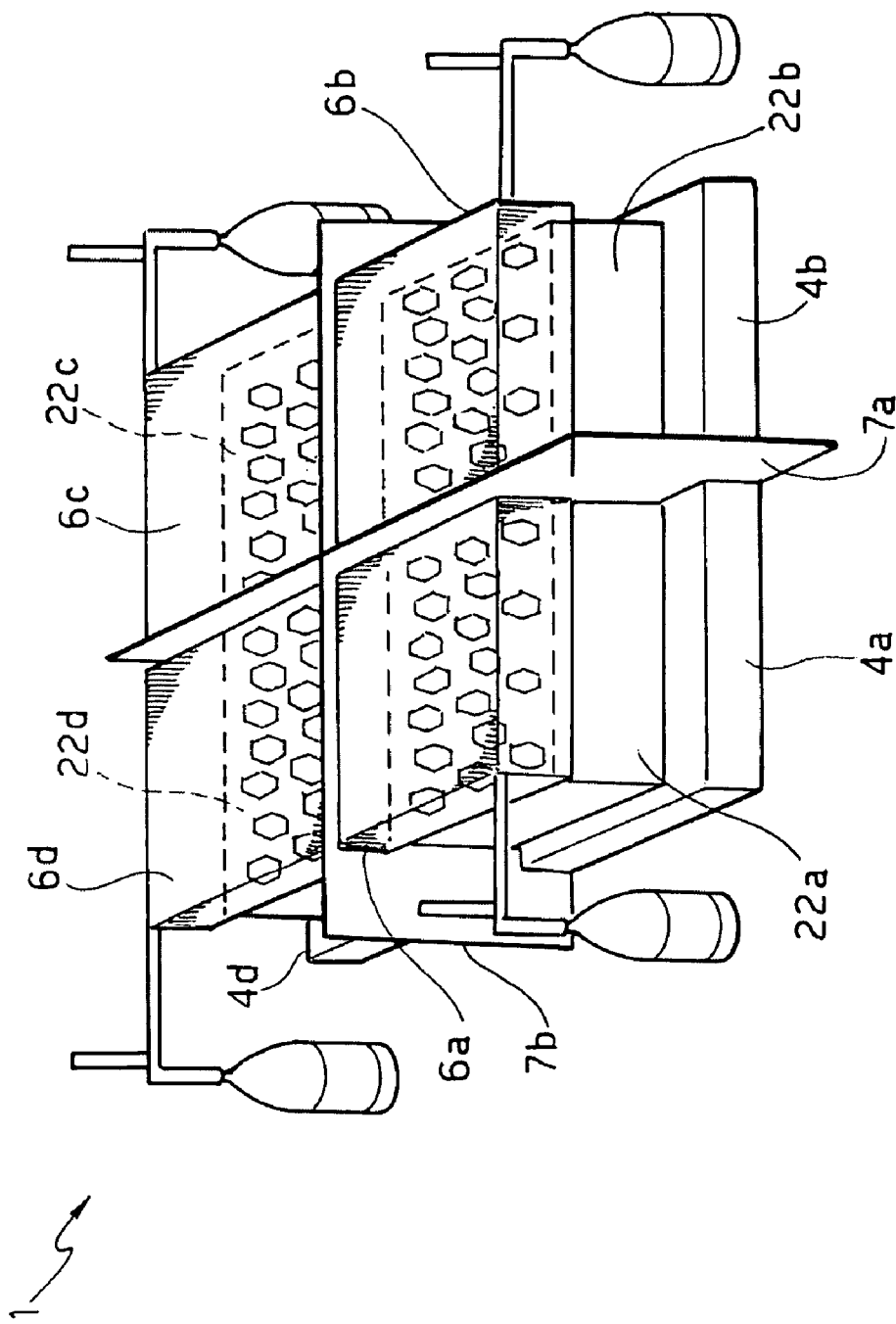

OPTICAL BIOSENSOR

BACKGROUND OF THE INVENTION

The present invention relates to a porous-matrix optical biosensor. In particular, the present invention relates to an optical biosensor with porous matrix constituted by anodized porous alumina connected to a detector, preferably a photodiode, for detection of the signal. The present invention moreover relates to a biosensor having an optical detector integrated with a porous matrix other than porous alumina, such as for example porous silicon.

A biosensor is a device capable of detecting a chemical or biochemical variable (analyte) by means of a biological component (biomediator), which, being immobilized on a matrix/substrate, functions as interface with a transducer. The transducer, which is constituted by the sensitized matrix and by a detector, is capable of transforming the chemico-physical signal deriving from the interaction between the biomediator and the analyte into a measurable physical (i.e., electrical) signal, which depends upon the variable analysed. The detector is able to measure the physical signal both in purely qualitative terms and in quantitative terms.

An optical biosensor is a device capable of measuring the luminescence—whether chemiluminescence or biolumines-cence—emitted during the interaction between the biomediator and its corresponding biological variable. Said interaction entails, in fact, occurrence of a chemical reaction which brings about the passage of one of the species involved in the reaction into an electronically excited state. Decay of said species from the excited state to the fundamental state brings about emission of photons (hv), the measurement of which supplies an indication not only of the presence but also of the amount of the analyte being measured.

The essential characteristics of biosensors are the sensitivity and the selectivity that the biological component is able to provide, in conjunction with the simplicity of use and the versatility that derives from the method of transduction chosen, which is usually compatible with specifications of low-cost miniaturizability.

The biomediators or biological systems used may be enzymes (e.g., luciferase), antibodies, biological membranes, bacteria of a wild strain or genetically modified bacteria (e.g., natural or recombinant bioluminescent bacteria), cells, animal or vegetable tissues; these interact directly or indirectly with the analyte to be determined and are responsible for the specificity of the sensor. The biomediator interacting with the analyte brings about a variation in one or more chemico-physical parameters of the species involved, giving, for example, rise to a chemiluminescent or bioluminescent reaction with corresponding emission of photons (hv).

The substrates used for immobilization of the biomediator can be constituted by various materials. Amongst the currently used ones there can mentioned silica gel, agarose, polymeric compounds such as, for example, polystyrene or polyacrylates, natural fibres such as silk, or else glass (micro)spheres.

The areas of application of biosensors are very wide and range from the medico-diagnostic sector to the environmental and foodstuff sectors.

In the foodstuff sector, biosensors can be used for determining chemical substances that may function as indicators, for example, of the microbial pollution present in a foodstuff or of the deterioration of the latter, for example caused by processes of oxidation. It is moreover possible to detect traces of contaminating chemical compounds, toxins, or else additives, preservatives, etc.

Also the applications in the environmental sector are extremely numerous for determining the presence of pesticides, hydrocarbons, and toxic gases. In many cases, on account of the need to detect levels of concentration that fall below the range of detection of the biosensor, the latter has been coupled, in the case of electrical transduction, to electronic amplifiers.

SUMMARY OF THE INVENTION

The purpose of the present invention is to provide an optical biosensor having a structure such as to facilitate the contacts between the sensitized porous matrix and the detector—i.e., to facilitate the functionality of the transducer—with consequent advantages in the detection of the signal generated by the transducer as a function of the interaction between the biomediator and the analyte.

According to the invention, the above purpose is achieved thanks to the solution recalled specifically in the ensuing claims, which are understood as forming an integral part of the present description.

In the currently preferred embodiment, the invention relates to an optical biosensor having as matrix (substrate), a material with porous structure, preferably anodized porous alumina, on which the biomediator is immobilized.

BRIEF DESCRIPTION OF THE DRAWINGS

Further characteristics and advantages of the biosensor according to the present invention will emerge clearly from the ensuing detailed description, provided purely by way of non-limiting example, with reference to the annexed drawings, in which:

FIG. 6 reproduces a further embodiment of the invention.

DETAILED DESCRIPTION OF THE INVENTION

Figure 1:
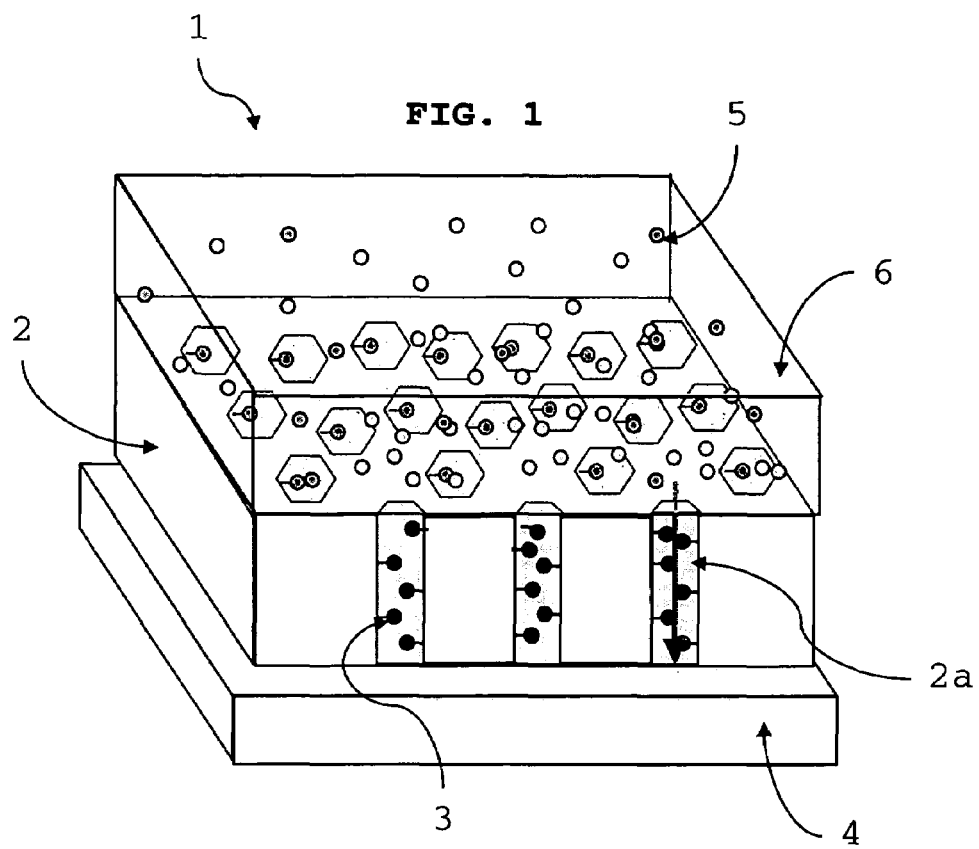
FIG. 1 represents an optical biosensor according to the invention.

With reference to FIG. 1, number 1 designates, as a whole, the optical biosensor. The biosensor 1 comprises a matrix or supporting structure 2 made of anodized porous alumina, inside the pores 2a of which there is immobilized the biomediator 3, which is able to react with the analyte 5 contained in the solution to be analysed 6. The porous matrix 2 is connected to, and preferably integrated with, an optical detector 4, capable of measuring the signal—emission of photons hv—generated by the reaction between the biomediator 3 and the analyte 5. The photons emitted during the reaction between the biomediator and the analyte are correlated, when the biomediator is not in conditions of saturation, to the amount of analyte present in the solution 6.

The innovative aspect of the present patent is represented by the use of a porous matrix 2 consisting of porous alumina obtained via a process of anodization of a film of high-purity aluminium or of a film of aluminium adhering to substrates such as glass, quartz, silicon, tungsten, etc.

The peculiar characteristics of anodized porous alumina are outlined in what follows. In the first place, the regularity of the pores bestows upon the material particular optical properties; in fact, the structural periodicity of the aforesaid material enables alternation of means with different dielectric constants, producing a photonic band gap that does not enable propagation of light radiation in a specific band of wavelengths and in certain directions, with consequent narrowing of the emission lobe of the outcoming light. In addition, the porous surface brings about a considerable increase in the area of possible contact. The latter aspect favours substantially the process of immobilization of the biomediator, which can reach higher concentrations per unit area as compared to the use of a compact smooth structure.

The dimensions and number of pores can be controlled by varying the conditions of anodization of metallic aluminium.

The choice of metallic aluminium as a starting material presents a major advantage: it can be deposited on any surface using evaporation techniques and be subsequently anodized. In this way, it is possible to deposit a layer of aluminium—subsequently subjected to anodization—directly on an optical detector (for example, a photodiode), so guaranteeing a further miniaturization of the biosensor.

The choice of porous alumina as a matrix further enables the use of photolithographic techniques followed by chemical etching, which enable the generation of any three-dimensional or two-dimensional structure of the matrix.

The subsequent opening of the pores of the alumina matrix enables treatment of the matrix as a true membrane and facilitates formation of the electrical contacts in the transducer.

Figure 2:
FIG. 2 reproduces two photographs obtained with the scanning electronic microscope of a cross section and a front section of a matrix of anodized porous alumina.
Figure 2:
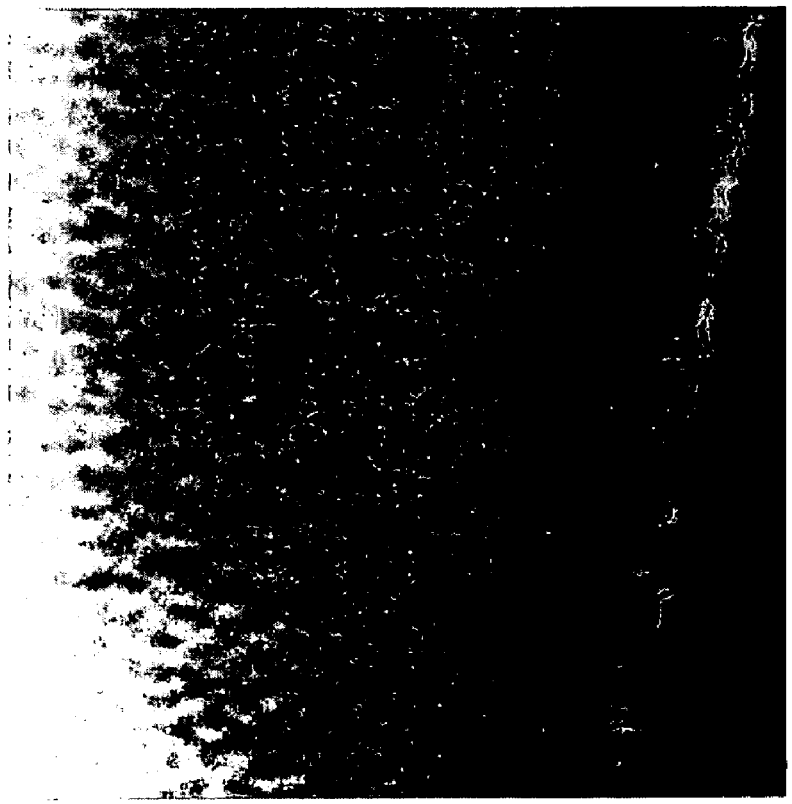

FIG. 2 illustrates, purely by way of example, a portion of a film of porous alumina obtained via anodic oxidation of an aluminium film. As may be noted, the layer of alumina is formed by a series of adjacent cells of a substantially hexagonal shape, each having a straight central hole which constitutes a hole substantially perpendicular to the surface of the underlayer (FIG. 2a).

As per the known art, the film of porous alumina can be developed with controlled morphology by appropriately choosing the electrolyte and the physical, chemical and electrochemical parameters of the process.

Briefly, the first step for integration of a photodiode to the biosensor is the deposition of an aluminium layer on an underlayer, the latter being, for example, made of silicon on which there have previously been inserted nanoclusters made of gold. The preferred techniques for deposition of the layer of aluminium are thermal evaporation via e-beam, and cathodic sputtering. The step of deposition of the aluminium layer is followed by a step of anodization of the layer itself. The process of anodization of the layer can be carried out using different electrolytic solutions according to the size and distance of the pores that are to be obtained. In order to obtain a highly regular structure, of the same type as the one represented in FIG. 2, it becomes necessary to carry out subsequent anodization processes, and, in particular, at least:

i) a first anodization;
ii) a step of reduction, via chemical etching, of the irregular film of alumina by means of acidic solutions; and
iii) a second anodization of the part of the film of alumina not eliminated during the step of chemical etching.

The etching step referred to in point ii) is important for defining on the residual part of alumina preferential areas of growth of the alumina itself in the second anodization step.

If the operations of etching ii) and anodization iii) are carried out a number of times, the structure improves until it becomes very uniform, as highlighted schematically in FIG. 2, where the film of alumina is regular.

The regular structure of porous alumina can be developed with controlled morphology by appropriately choosing the electrolyte and the physical, chemical and electrochemical parameters of the process: in acidic electrolytes (such as phosphoric acid, oxalic acid and sulphuric acid with concentrations of 0.2-1.2M) and in adequate process conditions (voltage of 40-200 V, current density of 5-10 mA/cm$^2$, stirring, and temperature of 0-4° C.), it is possible to obtain porous films presenting a high level of regularity. The diameter of the pores and the depth of the film may be varied; typically, the diameter is 50-500 nm and the depth 1-200 µm.

In the present invention, as a signal detector, and hence in the case in point as optical-signal detector, any system sensitive to light, such as a photodiode, may be used, where by the term "photodiode" is meant a photodiode formed by two or more sections.

Figure 3:
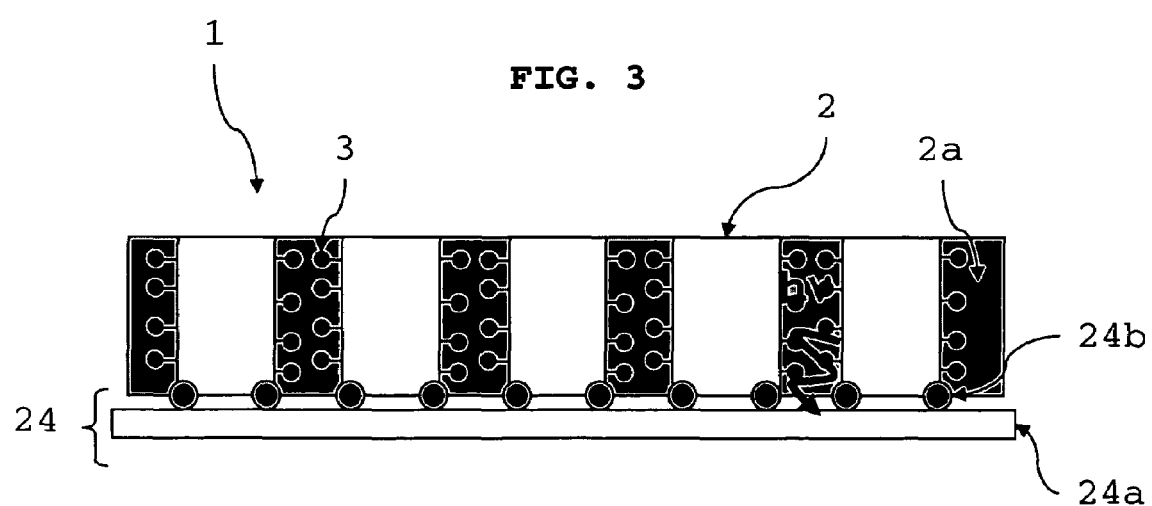
FIG. 3 illustrates the structure of an optical biosensor according to the invention.
Figure 4:
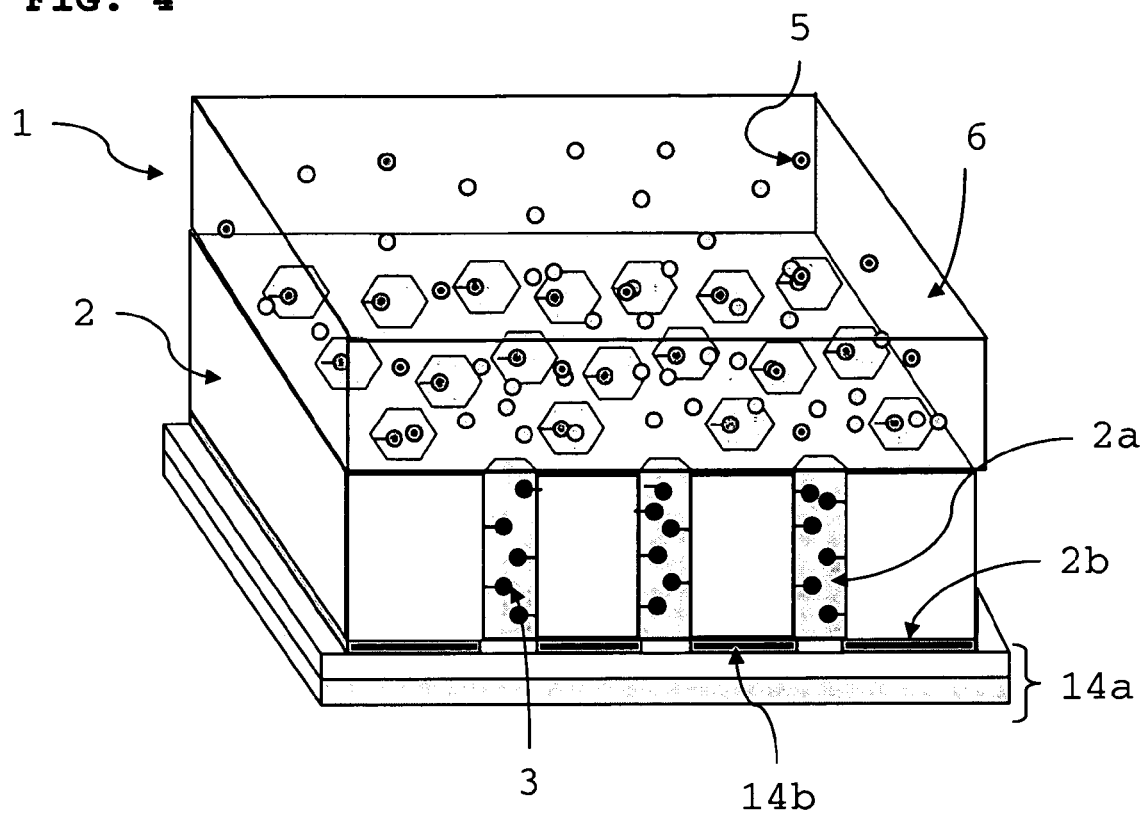
FIG. 4 represents an optical biosensor according to the invention coupled to a photodiode.

Alternatively, as detectors it is possible to use any light-sensitive means integrated with the porous matrix. By way of example, amongst the techniques that enable this integration between the optical detector and the porous matrix the following may be mentioned:

the nanopatterning technique, which envisages a process of deposition of a metal on the bottom portion of the porous matrix for a better adhesion of the photodiode to the matrix, as illustrated schematically in FIG. 4; and the integration technique, which envisages deposition on a silicon substrate of gold nanoclusters and then of the porous matrix (FIG. 3).

In the embodiment illustrated in FIG. 4, the biosensor, which is designated, as a whole, by the reference number 1, consists of a matrix of anodized porous alumina 2, inside the pores 2a of which the biomediators 3 specific for the analyte 5 contained in the solution to be analysed 6, are immobilized. The detector 14 of the light signal emitted by the interaction between the biomediator 3 and the analyte 5 is constituted by a photodiode 14a and a metal layer 14b adhering on the bottom surface 2b of the porous matrix for the purpose of improving the transmission of photons hµ between the matrix and the photodiode.

FIG. 3 represents another embodiment of the present invention. The matrix 2 of anodized porous alumina—inside the pores 2a of which the biomediator 3 is immobilized—is in contact with the detector 24 constituted by a series of metal nanoclusters 24b, preferably gold nanoclusters, deposited on a silicon substrate 24a so that the photons hv emitted during the biomediator-analyte interaction will be absorbed by the detector formed by the metal-silicon junction and will be detected by measuring the electrical potential at the junction.

Other optical detectors that can advantageously be used for the embodiment of the present invention may be represented by polymeric photodiodes, such as, for example, LEP (Light-Emitting Polymer) optical sensors or OLED (Organic Light-Emitting Diode) optical sensors. The use of these polymeric photodiodes presents the major advantage of employing flexible structures with high biocompatibility. An advantageous example of a possible application of this particular embodiment of the present invention is provided by the integration of this biosensor in a diagnostic instrument such as an endoscope; the endoscope presents the biosensor throughout its length for instantaneous monitoring of the analyte in question along an extensive stretch of the organ being examined.

An alternative embodiment of the present invention envisages the possibility of integrating the optical detector with biosensors formed by a porous matrix other than porous alumina; by way of example, reference will be made to porous silicon.

Figure 5:
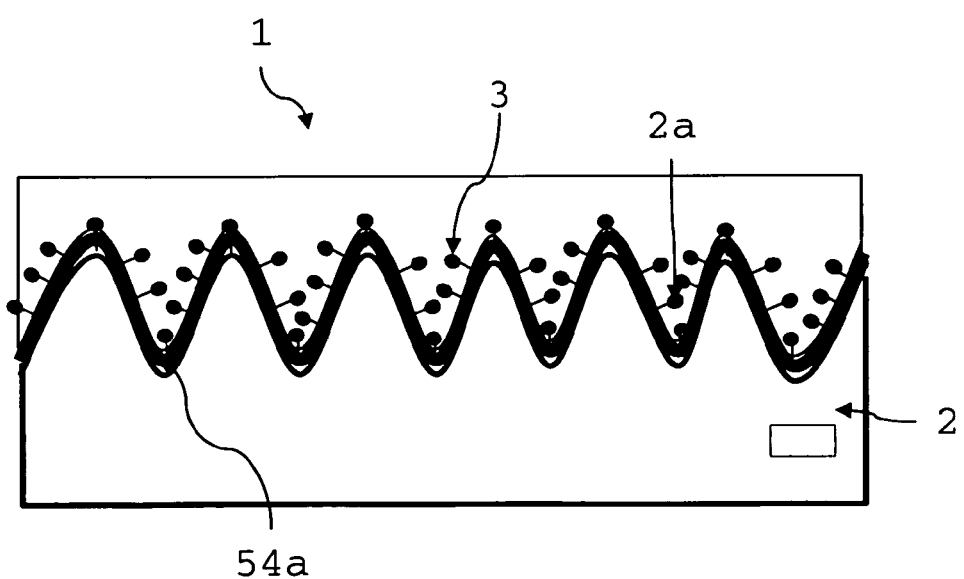
FIG. 5 illustrates an optical biosensor having a porous matrix consisting of porous silicon.

The porosity of the silicon matrix can be varied according to the biological species (biomediators) and hence to the analytes that are to be detected. With reference to FIG. 5, the porous silicon 2 is coated by electrochemical deposition with a continuous metal layer 54a (for example, gold) so as to function itself as a photodiode 54, there being created a Schottky junction. The internal walls of the pores 2a of porous silicon, coated with metal 54a, also function as substrate for the biomediator 3, which is immobilized thereon. In order to immobilize the mediator the techniques described hereinafter are used.

When the reaction between the biomediator and the analyte brings about emission of photons, these are immediately absorbed by the photodiode 54 constituted by the metal-silicon junction and are detected by measuring the electrical potential that is set up between the silicon and the metal.

The main advantage of the above embodiment of the present invention is provided by the complete integration of the porous matrix sensitized with the biomediator and of the optical sensor, with evident advantages in terms of design, reduction of the technological process steps and of the costs of the devices themselves.

In a particular embodiment represented schematically in FIG. 6, it is possible to provide an optical biosensor according to the present invention having the porous matrix divided into two or more sections, so that each section will be sensitized with a different biomediator capable of detecting one specific analyte and the biosensor as a whole shall be capable of detecting simultaneously two or more analytes of interest, thus obtaining a so-called "lab-on-chip". The individual sections are separate from one another, and, through exploitation of a system of injectors and reservoirs, the efficiency of the biomediators is guaranteed.

With reference to FIG. 6, the porous matrix 2 of the biosensor 1 is divided into four sections 22a, 22b, 22c and 22d sensitized with four different biomediators 3 which are specific for different analytes. This division is obtained by means of barriers 7a and 7b, which enable the four environments 6a, 6b, 6c, 6d for the biomediator-analyte reaction to be kept separate. Also the detector is divided according to the partitions of the porous matrix so that the signals of the biomediator-analyte interactions of the four reaction environments may be processed separately, but simultaneously, by the detectors 64a, 64b, 64c and 64d, and a multiparametric analysis can be conducted.

The immobilization of the biomediator (whether this be an enzyme or a complex biological organism) on the porous matrix can be achieved by a wide range of techniques. By way of non-limiting example, the following may be mentioned:

formation of non-covalent bonds (e.g., hydrogen bonds, Van der Waals bonds) between the biomediator and the porous matrix possibly functionalized in an appropriate manner;

micro-encapsulation through the use of membranes of porous alumina capable of entrapping the biomediator;

formation of covalent bonds between the biomediator and the porous matrix, optionally appropriately functionalized; and cross-bonding with a bifunctional chemical compound capable of setting up a chemical bond between the matrix on the one hand and the biomediator on the other (this method can be used in concomitance with other immobilization techniques, such as absorption and micro-encapsulation).

The techniques that envisage the use of non-covalent bonds for immobilization of the biomediator to the matrix are preferable, in so far as they do not require any chemical modification of the biomediator. In this case, the surface of the porous alumina is preferably impregnated with any compound capable of increasing adhesion of the biomediator to the surface itself. An example of one of these compounds is given by a polylysine peptide, which, by being adsorbed on the hydrophilic surface of the alumina, is then capable of "co-ordinating" with the biomediator exploiting the presence of $-NH_2$ groups on its side chain and hence giving rise to hydrogen bonds and/or of Van der Waals bonds with the hydrophilic groups of the biomediator. A second example of a compound capable of increasing adhesion of the biomediator to the alumina matrix is polyprenyl phosphate; the phosphate group functions as an anchor capable of being adsorbed on the alumina, and the prenylenic tail—by rendering the alumina surface more hydrophobic—will favour the formation of non-covalent bonds between the matrix thus functionalized and the biomediator.

Of course, without prejudice to the principle of the invention, the details of construction and the embodiments may vary respect to what is described and illustrated herein, without thereby departing from the scope of the invention.

What is claimed is:

1. A biosensor comprising:
   a porous matrix in the form of a body with a bottom planar face presenting a plurality of through pores opening on said bottom face;
   biomediator immobilized on said matrix; and
   a signal detector connected to said matrix, the signal detector being in the form of a flattened planar element having an upper surface facing said bottom face of the matrix body,
   wherein said porous matrix is integrated on said detector,
   wherein said signal detector comprises a discontinuous metal layer in the form of metal nano-clusters and a silicon layer, wherein said discontinuous metal layer is set between said porous matrix and said silicon layer.

2. The biosensor according to claim 1, wherein said porous matrix is an anodized porous alumina.

3. The biosensor according to claim 2, wherein the anodized porous alumina is an anodized aluminum film.

4. The biosensor according to claim 3, wherein the anodized porous alumina is an anodized and chemically etched aluminum film.

5. The biosensor according to claim 4, wherein the anodized porous alumina is a twice anodized and chemically etched aluminum film.

6. The biosensor according to claim 3, wherein the anodized porous alumina is a twice anodized and twice chemically etched aluminum film.

7. The biosensor according to claim 1, wherein the discontinuous metal layer is gold, and the discontinuous metal layer is deposited on the silicon layer.

8. The biosensor according to claim 1, wherein said biomediator is immobilized on said porous matrix by non-covalent bonds between said biomediator and said porous matrix; micro-encapsulation of the biomediator on said porous matrix; covalent bonds between said biomediator and said porous matrix; and/or cross-bonding with a bifunctional chemical compound capable of forming a bond between said porous matrix and said biomediator.

9. The biosensor according to claim 8, wherein said biomediator is immobilized on said porous matrix by the bifunctional chemical compound.

10. The biosensor according to claim 1, wherein said porous matrix comprises one or more sections.

11. The biosensor according to claim 10, wherein the detector comprises one or more sections corresponding to said sections of the porous matrix.

12. The biosensor according to claim 8, wherein biomediator comprises one or more sections corresponding to said sections of the porous matrix, wherein the one or more sections of the biomediator different biomediators, specific for different analytes.

* * * * *